(12) United States Patent
Anderson

(10) Patent No.: US 10,052,455 B1
(45) Date of Patent: Aug. 21, 2018

(54) MEDICAL DEVICE PACKAGE

(71) Applicant: Covidien LP, Mansfield, MA (US)

(72) Inventor: Christopher Anderson, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/431,339

(22) Filed: Feb. 13, 2017

(51) Int. Cl.
*A61M 25/00* (2006.01)
(52) U.S. Cl.
CPC .................. *A61M 25/002* (2013.01)
(58) Field of Classification Search
CPC ............ A61M 25/002; A61M 25/0023; A61M 25/0021; A61B 50/30; A61F 2/0095
USPC .................. 206/364, 363, 370, 438
See application file for complete search history.

(56) References Cited

U.S. PATENT DOCUMENTS

| 3,514,171 A | | 5/1970 | McGaha |
| 4,607,746 A | * | 8/1986 | Stinnette ............. A61M 25/002 206/363 |
| 4,688,674 A | | 8/1987 | Stirtz |
| 4,886,500 A | | 12/1989 | Lazarus |
| 5,098,391 A | * | 3/1992 | Pantages ................ A61B 50/33 206/563 |
| 5,344,011 A | * | 9/1994 | DiBernardo ........ A61M 25/002 206/364 |
| 5,526,928 A | * | 6/1996 | Yabe ...................... A61B 1/121 206/363 |
| 6,068,121 A | | 5/2000 | McGlinch |
| 7,334,678 B2 | * | 2/2008 | Kesler ................. A61M 25/002 206/303 |
| 7,461,741 B2 | * | 12/2008 | State .................... A61M 25/002 206/364 |
| 7,640,714 B2 | * | 1/2010 | Waller ................ A61M 25/002 206/364 |
| 8,020,703 B2 | | 9/2011 | List et al. |
| 8,239,040 B2 | | 8/2012 | Geistert |
| 8,702,619 B2 | | 4/2014 | Wang |
| 9,789,277 B2 | * | 10/2017 | Suzuki ............ A61M 25/09041 |
| 2005/0061698 A1 | * | 3/2005 | Delaney .............. A61M 25/002 206/364 |
| 2008/0058766 A1 | * | 3/2008 | Gilson ...................... A61F 2/01 604/523 |
| 2008/0183181 A1 | * | 7/2008 | Treacy .................... A61L 2/206 606/108 |
| 2009/0090650 A1 | * | 4/2009 | Wells ..................... A61B 50/30 206/571 |
| 2012/0022470 A1 | * | 1/2012 | Kuniyasu ............ A61M 25/002 604/265 |
| 2012/0037525 A1 | * | 2/2012 | Peck ...................... A61L 2/206 206/364 |
| 2012/0261290 A1 | * | 10/2012 | Limjaroen .......... A61M 25/002 206/364 |
| 2015/0246202 A1 | * | 9/2015 | Mcnamara .......... A61M 25/002 206/364 |
| 2016/0001037 A1 | * | 1/2016 | Hong .................... B65H 75/28 604/544 |

* cited by examiner

*Primary Examiner* — Steven A. Reynolds
(74) *Attorney, Agent, or Firm* — Shumaker & Sieffert, P.A.

(57) ABSTRACT

In some examples, a medical device package includes an elongated tube member defining a lumen, wherein the lumen is configured to receive an elongated medical device. The elongated tube member defines a non-concentric shape, such as a shape that includes a plurality of clockwise turns and a plurality of counterclockwise turns.

28 Claims, 12 Drawing Sheets

MEDICAL DEVICE PACKAGE

TECHNICAL FIELD

This disclosure relates to packages for medical devices.

BACKGROUND

Elongated medical devices, such as catheters, may be packaged in a relatively compact configuration prior to use. For example, a catheter may be stored in a coiled configuration for shipment and storage prior to use by a clinician during a medical procedure.

SUMMARY

This disclosure describes example medical device packages that are configured to store elongated medical devices in a configuration that may help facilitate the later-introduction of the medical device in a patient. An elongated medical device may, in some cases, assume the shape in which it is stored in a medical device package. In some cases, the assumed shape may impact the ease of delivery of the medical device in a patient. For example, the elongated medical device may be stored in a configuration in a package that imparts a curvature to the elongated medical device. This curvature may adversely impact the navigability of the elongated medical device within vasculature of a patient, such as by causing a "whipping" effect during rotation of the medical device. The medical device packages described herein are configured to store elongated medical devices in a configuration that may help minimize or even eliminate the adverse effects of medical device storage on the navigability of the medical device compared to medical device packages that store elongated medical devices in a coiled configuration. For example, example medical device packages described herein may reduce whipping by packaging the elongated medical device in a shape that reduces the tendency of the elongated medical device to whip.

In some examples, a medical device package is configured to store a medical device in a shape that includes both clockwise and counterclockwise turns so that the elongated medical device does not conform to a loop shape including only clockwise turns or only counterclockwise turns.

Clause 1: In one example, a medical device package includes an elongated tube member defining a lumen, wherein the lumen is configured to receive an elongated medical device, and wherein the elongated tube member defines a shape that includes a plurality of clockwise turns and a plurality of counterclockwise turns.

Clause 2: In some examples of the medical device package system of clause 1, the package further comprises an attachment element configured to hold the elongated tube member at two or more locations such that the elongated tube member defines the shape that includes the plurality of clockwise turns and the plurality of counterclockwise turns.

Clause 3: In some examples of the medical device package system of clause 2, the attachment element comprises two or more clips configured to connect to an outer wall of the elongated tube member.

Clause 4: In some examples of the medical device package system of any of clauses 2-3, a distance between a first location of the two or more locations and a second location of the two or more locations is about 10 centimeters (cm) to about 20 cm along the elongated tube member, and the first location and the second location are adjacent to each other.

Clause 5: In some examples of the medical device package system of any of clauses 1-4, the shape is a serpentine shape.

Clause 6: In some examples of the medical device package system of clause 5, the serpentine shape comprises two or more turns, and a radius of curvature for each turn of the two or more turns is more than two centimeters and less than fifteen centimeters.

Clause 7: In some examples of the medical device package system of any of clauses 5-6, the radius of curvature for each turn of the two or more turns is more than four centimeters and less than eight centimeters.

Clause 8: In some examples of the medical device package system of any of clauses 1-7, the shape includes a plurality of alternating clockwise turns and counterclockwise turns.

Clause 9: In some examples of the medical device package system of any of clauses 1-8, a clockwise turn of the plurality of clockwise turns is adjacent to a counterclockwise turn of the plurality of counterclockwise turns.

Clause 10: In some examples of the medical device package system of any of clauses 1-9, the shape is a figure-eight shape.

Clause 11: In some examples of the medical device package system of any of clauses 1-10, the elongated tube member comprises a polymer.

Clause 12: In some examples of the medical device package system of clause 11, the polymer is high-density polyethylene.

Clause 13: In some examples of the medical device package system of any of clauses 1-12, the elongated tube member defines two or more loops that do not overlap.

Clause 14: In some examples of the medical device package system of any of clauses 1-13, the elongated tube member comprises a length of about 100 centimeters (cm) to about 300 cm.

Clause 15: In some examples of the medical device package system of any of clauses 1-14, the lumen has a diameter of less than about 3 millimeters (mm).

Clause 16: In some examples of the medical device package system of any of clauses 1-15, the medical device package further comprises the elongated medical device received within the elongated tube member.

Clause 17: In some examples of the medical device package system of clause 16, the elongated medical device comprises a catheter.

Clause 18: In some examples of the medical device package system of any of clauses 16-17, the elongated medical device is fully received within the elongated tube member.

Clause 19: In some examples, a medical device package includes an elongated tube member defining a lumen, wherein the lumen is configured to receive an elongated medical device, and wherein the elongated tube member defines a non-concentric shape.

Clause 20: In some examples of the medical device package of clause 19, the medical device package further comprises an attachment element configured to hold the elongated tube member at two or more locations such that the elongated tube member defines the non-concentric shape.

Clause 21: In some examples of the medical device package of any of clauses 19-20, the non-concentric shape is a serpentine shape or a figure-eight shape.

Clause 22: In some examples of the medical device package of any of clauses 19-21, the elongated tube member defines two or more loops that do not overlap.

Clause 23: In some examples of a medical device package configured to store an elongated medical device, the medical device package comprises an elongated tube member defining a lumen, wherein the lumen is configured to receive the elongated medical device; and attachment means connecting to the elongated tube member, wherein the attachment means is configured and positioned such that elongated tube member defines a shape that includes a plurality of clockwise turns and a plurality of counterclockwise turns.

Clause 24: In some examples, a method includes forming a medical device package comprising an elongated tube member defining a lumen, wherein the lumen is configured to receive an elongated medical device, and wherein the elongated tube member defines a shape that includes a plurality of clockwise turns and a plurality of counterclockwise turns.

Clause 25: In some examples of the method of clause 24, forming medical device package comprises attaching an attachment element to the elongated tube member to hold the elongated tube member in the shape that includes the plurality of clockwise turns and the plurality of counterclockwise turns.

Clause 26: In some examples of the method of any of clauses 24-25, the shape is a serpentine shape or a figure-eight shape.

Clause 27: In some examples of the method of any of clauses 24-26, the elongated tube member defines two or more loops that do not overlap.

Clause 28: In some examples of the method of any of clauses 24-27, the method further comprises introducing the elongated medical device in the lumen of the elongated tube member.

The details of one or more examples are set forth in the accompanying drawings and the description below. Other features, objects, and advantages will be apparent from the description and drawings, and from the claims.

DETAILED DESCRIPTION

Figure 1:
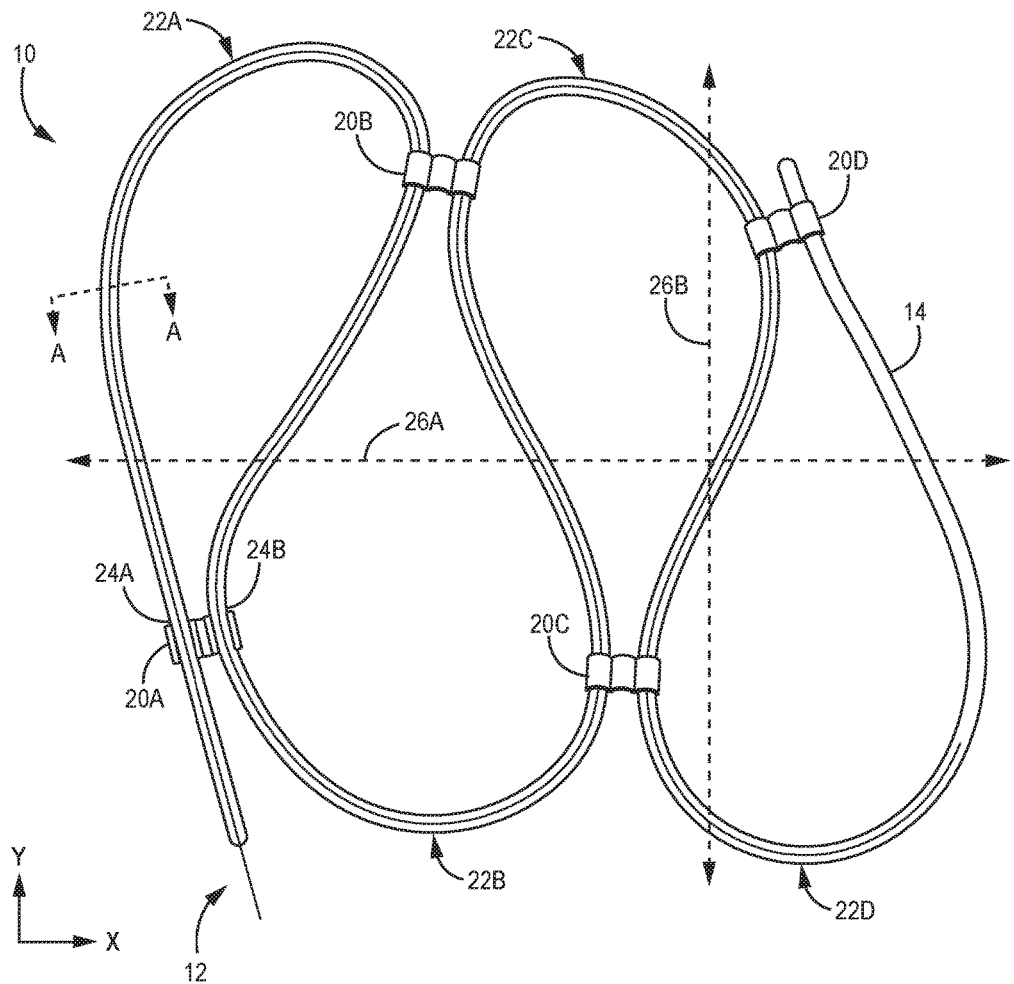
FIG. 1 illustrates an example medical device package configured to hold an elongated medical device in a serpentine shape.

Elongated medical devices, such as catheters, may be packaged for shipment and storage after manufacture and before being used in a medical procedure. An elongated medical device may be packaged in a configuration other than a linear configuration (e.g., where the device may be held in a straight configuration) in order to provide for more efficient storage of the elongated medical device, e.g., by storing the medical device in a package having a footprint with at least one smaller dimension than the linear configuration of the medical device. For example, the medical device may be stored in a package having a smaller length than the total length of the medical device, measured along a longitudinal axis of the medical device. In addition, storing the elongated medical device in a non-linear configuration may help reduce shipping costs, provide for easier manipulation (less awkward) of the medical device package, or any combination thereof.

The medical device package may also help isolate the elongated medical device from the surrounding environment, e.g., to help protect the structural integrity of the medical device, to help prevent contamination of the elongated medical device during shipping and/or storage, or to both help protect the structural integrity of the medical device and to help prevent contamination of the medical device. Depending on the shape and configuration of the packaging, two or more elongated medical devices may be placed into a single outer container for shipment and/or storage.

In some cases, the shape an elongated medical device is held in by medical device packaging may affect the performance of the elongated medical device. For example, the shape an elongated medical device is held in in the packaging may impact the at-rest shape assumed by the elongated medical device when it is removed from the packaging. This may be due to, for example, the type of materials from which the elongated medical device is formed, heat setting of the medical device in the packaging shape during sterilization of the medical device while it is in the packaging, or the like. The at-rest shape of the elongated medical device can be, for example, the shape of the medical device in the absence of any forces applied to the medical device by a user or an external apparatus. As an example of how the shape elongated medical device is held in by medical device packaging may affect the performance of the elongated medical device, some packaging shapes may adversely impact the navigability of the elongated medical device in the vasculature of the patient, e.g., by increasing the likelihood and severity of whipping of the medical device.

To reduce the impact the medical device packaging has on the performance of an elongated medical device that it stores, e.g., to reduce likelihood of whipping for the elongated medical device, an elongated medical device may be packaged in an elongated tube member of a medical device package, where the elongated tube member may hold the elongated medical device in a non-concentric shape. A concentric shape includes a plurality of circles or arcs that share the same center or approximately the same center. In some examples, the non-concentric shape includes a plurality of clockwise turns and a plurality of counterclockwise turns, such as a serpentine shape. By holding the elongated tube member in such a non-concentric shape, the package may improve the responsiveness of the distal portion of the medical device to rotational force applied to the proximal portion of the medical device by a clinician, as discussed in further detail below. Example non-concentric shapes that include a plurality of clockwise turns and a plurality of counterclockwise turns are described with respect to FIGS. 1, 5, 7, and 8.

FIG. 1 illustrates an example medical device package 10 configured to hold an elongated medical device 12 in a shape that includes a plurality of clockwise turns 22A and 22C and a plurality of counterclockwise turns 22B and 22D. In the example shown in FIG. 1, the shape is a serpentine shape, an S-shape, or a meandering shape. In other examples, however, the shape may be different. Additional example shapes are described with respect to FIGS. 5, 7, and 8.

In the example shown in FIG. 1, medical device package 10 includes elongated tube member 14 and attachment elements 20A-20D. Elongated tube member 14 defines a lumen configured to receive elongated medical device 12. As shown in FIG. 1, elongated medical device 12 is partially inside elongated tube member 14 and partially outside of elongated tube member 14. Although elongated medical device 12 is shown partial inside and outside of elongated tube member 14 in FIG. 1, elongated medical device 12 may be fully inside elongated tube member 14 or completely outside elongated tube member 14. For example, elongated tube member 14 may be sized to fully receive the entire length of elongated medical device 12, the length being measured in along the longitudinal axis of elongated medical device 12. Thus, elongated medical device 12 may be positioned fully inside of elongated tube member 14 during shipment and storage. In some examples, elongated tube member 14 and/or elongated medical device 12 may include a length of about 100 centimeters (cm) to about 300 cm. However, elongated tube member 14 and/or elongated medical device 12 may have other lengths in other examples, which may vary based on medical device.

Although examples in which elongated medical device 12 is positioned fully inside of elongated tube member 14 during shipment and storage, when an assembly including package 10 and device 12 is fully assembled, are primarily described herein, in other examples, elongated tube member 14 may be sized to receive only a part of the length of elongated tube member 14. This may allow a part of elongated medical device 12 (e.g., a part including a distal end or a proximal end) to extend from an end of elongated tube member 14 when medical device 12 is packaged within elongated tube member 14. A clinician may grasp the part extending from the end of elongated tube member 14 in order to retrieve medical device 12 from the lumen of elongated tube member 14.

An end of elongated medical device 12 may be placed into elongated tube member 14, and elongated medical device 12 may be pushed into elongated tube member 14 until all of elongated medical device 12 is inside elongated tube member 14. Before being used in a medical procedure that may include introduction of elongated medical device 12 into the vascular system of a patient, elongated medical device 12 may be pulled out of elongated tube member 14. During use in a medical procedure, elongated medical device 12 may be partially or fully outside of elongated tube member 14.

Elongated medical device 12 includes any suitable elongated medical member that is configured for insertion into a patient, such as a catheter, an electrical stimulation lead, or a guide wire. Although not shown in FIG. 1, in some examples, elongated medical device 12 may include other components, such as, but not limited to, a hub, a luer fitting, a handle, and the like. These additional components may be housed within the lumen of elongated tube member 14 or may be positioned outside of elongated tube member 14 when the elongated medical member of elongated medical device 12 is fully housed within elongated tube member 14. For example, due to the size of a hub or handle being larger than the lumen of elongated tube member 14, the hub or handle may protrude from the end of elongated tube member 14 when the elongated medical member (e.g., the catheter body) of medical device 12 is housed within the lumen of elongated tube member 14 in the assembled configuration of package 10. The hub or handle, or other component at the end of the elongated medical member, may, for example, sit against or be spaced from an end of elongated tube member 14 when the elongated medical member of medical device 12 is housed within the lumen of elongated tube member 14 in the assembled configuration of package 10. This may facilitate the extraction of the elongated medical member of medical device 12 from elongated tube member 14 by providing a clinician with an easy way to grasp medical device 12 in order to apply a pulling force away from elongated tube member 14 to pull medical device 12 out of elongated tube member 14.

In some examples, elongated medical device 12 may be configured for insertion into the vascular system of the patient, including the blood vessels of the patient. For example, a clinician may insert a distal portion (including a distal end) of elongated medical device 12 into the vascular system of a patient during a medical procedure. The clinician may control the movement and rotation of a distal portion of elongated medical device 12 by moving and/or rotating a proximal portion of elongated medical device 12, where the proximal portion may remain outside the patient while the distal portion is inside the vasculature (or another body lumen) of the patient.

Elongated medical device 12 may be packaged for sterilization and shipping. Elongated medical device 12 may conform to or set into a shape or configuration of medical device package 10 in which elongated medical device 12 is stored. For example, during sterilization of elongated medical device 12, in which device 12 may be already be packaged in elongated tube member 14, elongated medical device 12 may be exposed to elevated temperatures, possibly causing elongated medical device 12 to heat-set and adopt the shape of the elongated tube member 14. Thus, in some cases, after elongated medical device 12 is removed from medical device package 10, elongated medical device 12 may continue to hold the shape of elongated tube member 14. Elongated medical device 12 may be relatively flexible, such that it may be manually manipulated into other shapes, but elongated medical device 12 may have a tendency to revert to the shape of elongated tube member 14 of medical device package 10.

When the distal portion of elongated medical device 12 is in a blood vessel, a clinician may attempt to orient the distal portion, e.g., to cause a distal tip of elongated medical device 12 to enter a side branch of the blood vessel. The clinician may, for example, apply a torsional force to the proximal portion of elongated medical device 12 try to rotate the distal portion of elongated medical device 12. The shape of the packaging for elongated medical device 12 may affect the responsiveness of elongated medical device 12 to such torsional force, even after elongated medical device 12 is removed from the packaging. For example, if elongated medical device 12 is packaged in a coiled configuration (e.g., a plurality of concentric circles), after medical device 12 is pulled from the package, medical device 12 may tend to remain at least partially coiled. This may cause the distal portion of elongated medical device 12 to not respond proportionally to the rotation of the proximal portion.

As the clinician moves and/or rotates the proximal portion of elongated medical device 12, the distal portion of elongated medical device 12 may not immediately or proportionally respond to the movement and/or rotation of the proximal portion. For example, the distal portion of elongated medical device 12 may rotate slowly in response to the rotational force applied to the proximal portion of elongated medical device 12, and then suddenly rotate more quickly, resulting in a jumping or skipping of the distal portion as the clinician rotates the proximal portion. This jumping, also known as whipping, may impede the clinician from quickly and accurately placing the distal portion of elongated medical device 12 at a desired location, which may increase the duration of time required to position elongated medical device 12 at a target site within vasculature of a patient. For example, the jumping of the distal portion in response to the rotational force may cause the distal tip may jump or skip past a desired side branch of a blood vessel. The jumping or skipping Elongated tube member 14 is configured to hold and package elongated medical device 12 in a shape that may reduce the likelihood and severity of whipping of elongated medical device 12 during a medical procedure, e.g., as compared to a medical device package that holds medical device 12 in concentric circles. In the example shown in FIG. 1, the shape includes a plurality of clockwise turns and a plurality of counterclockwise turns.

As depicted in FIG. 1, elongated tube member 14 may define successive turns 22A-22D of alternating directions such that elongated tube member 14 does not overlap on itself. The shape of elongated tube member 14, as depicted in FIG. 1, may include a plurality of alternating clockwise turns 22A and 22C and counterclockwise turns 22B and 22D. Turn 22A may be adjacent to turn 22B, turn 22B may be adjacent to turns 22A and 22C, and turn 22C may be adjacent to turn 22B and turn 22D. Elongated tube member 14 may include alternating turns because, for example, turn 22C may be clockwise and adjacent turn 22B and adjacent turn 22D may be counterclockwise.

Starting from the lower-left corner of FIG. 1 where elongated medical device 12 is shown to be partially outside of elongated tube member 14, elongated tube member 14 may first make clockwise turn 22A near a location held by attachment element 20B. Elongated tube member 14 may then make counter-clockwise turn 22B near locations held by attachment elements 20A, 20C. Elongated tube member 14 may then make clockwise turn 22C near locations held by attachment elements 20B, 20D. Elongated tube member 14 may then make counter-clockwise turn 22D near a location held by attachment element 20C. In some examples, elongated tube member 14 may include fewer or more turns than depicted in FIG. 1. Elongated tube member 14 may also include turns into or out of the page of FIG. 1 that may not necessarily be depicted in FIG. 1.

Turns 22A-22D may have any suitable radius of curvature, which may be selected based on the kink resistance of elongated medical device 12. For example, turns 22A-22D may each have a radius of curvature (measured along the inside curvature of tube member 14) that is greater than or equal to radius of curvature at which elongated medical device 12 kinks so as to help avoid imparting a kink to medical device 12 when it is stored in package 10. The kink resistance of elongated medical device 12 may be, for example, indicated by minimum bend radius (measured along the inside curvature of elongated medical device 12) that elongated medical device 12 can be bended without kinking it. In some examples turns 22A-22D defined by elongated tube member 14 have a radius of about 0.5 inches (approximately 12.7 millimeters (mm)) to about 5 inches (approximately 127 mm).

Each of turns 22A-22D may have the same radius of curvature in some examples. In other examples, however, at least two of the turns 22A-22D may have different radii of curvature. In some examples, a footprint of medical device package 10 may have width 26A in the x-axis direction of about 28 cm and height 26B in the y-axis direction of about 28 cm. Width 26A may be, for example, measured as the greatest linear distance between opposite edges of package 10 (e.g., the greatest distance between surfaces of elongated tube member 14 in the x-axis direction), and height 26B may similarly be measured as the greatest linear distance between opposite edges of package 10 (e.g., the greatest distance between surfaces of elongated tube member 14 in the y-axis direction). A height of medical device package 10, measured in the z-axis direction, may be based on cross-sectional dimension of elongated tube member 14, measured in a direction orthogonal to the longitudinal axis of elongated tube member 14. In some examples, to reduce the footprint of medical device package 10, elongated tube member 14 may be folded in half in the x-axis direction. For example, elongated tube member 14 may define a serpentine shape, and then may reverse back along the same serpentine shape to define medical package 10 having a reduced footprint. Folding elongated tube member 14 in half may reduce width 26A of medical device package 10.

Elongated tube member 14 may include any suitable material that is less flexible than elongated medical device 12, e.g., to structurally shield medical device 12, where the material may also help protect elongated medical device 12 from contamination. In some examples, elongated tube member 14 may include a polymer, such as, but not limited to, high-density polyethylene (HDPE).

Elongated tube member 14 may be held in the shape shown in FIG. 1 using any suitable technique. In some examples, elongated tube member 14 is relatively rigid (e.g., self-supporting) and can be hold the shape shown in FIG. 1 (or other shapes described herein) for packaging medical device 12 without the aid of any attachment elements. In the example shown in FIG. 1, however, medical device package 10 includes a plurality of attachment elements 20A-20D that are configured to hold elongated tube member 14 at two or more locations such that elongated tube member 14 defines a shape that includes a plurality of clockwise turns and a plurality of counterclockwise turns.

Although four attachment elements 20A-20D are shown in FIG. 1, medical device package 10 may also include any suitable number of attachment elements 20A-20D for holding elongated tube member 14 in the desired shape. The number of attachment elements 20A-20D may depend on, for example, the length of elongated tube member 14, the desired packaging shape of elongated tube member 14, the material from which elongated tube member 14 is formed, and the like. In some examples, medical device package 10 may include as few as one of attachment elements 20A-20D or more than four attachment elements 20A-20D.

Each of the attachment elements 20A-20D may have any suitable configuration. FIG. 1 depicts each of attachment elements 20A-20D as attached to elongated tube member 14 at two locations. For example, attachment element 20A may be attached to two locations 24A, 24B on elongated tube member 14. Attachment element 20A may be attached to only two locations, so locations 24A and 24B are adjacent, even though attachment element 20B is attached to elongated tube member 14 between locations 24A, 24B. In some examples, a distance along elongated tube member 14 (e.g., a length of elongated member 14) between location 24A and location 24B may be between about 10 cm and about 20 cm. As used herein, "about" a specific distance may include a tolerance of ten percent of the specific distance. Two of the locations for an attachment element may be adjacent if there are no other locations to which the attachment element is attached between the two locations. In other examples, one or more of attachment elements 20A-20D may be attached to elongated tube member 14 at one, three, four, or more locations along elongated tube member 14.

In some examples, each of attachment elements 20A-20D may be discrete components (e.g., separate from elongated tube member 14) configured to mechanically connect to elongated tube member 14. In addition to, or instead of, being separate from elongated tube member 14, some or all of attachment elements 20A-20D may be integral with or formed onto elongated tube member 14. Attachment elements 20A-20D may include many possible shapes and configurations, including a clip or a hook configured to attach to an outer wall of elongated tube member 14. In some examples, each of attachment elements 20A-20D may be adhered to elongated tube member 14 by an adhesive such as glue, epoxy, tape, paste, or any other suitable adhesive. In some examples, each of attachment elements 20A-20D may attach to elongated tube member 14 by mechanical means such as snapping, locking, clamping, friction fitting, and/or any other suitable means. In some examples, medical device package 10 may include attachment elements 20A-20D without elongated tube member 14 such that attachment elements 20A-20D connect to elongated medical device 12 at two or more locations to hold elongated medical device 12 defines a shape that includes a plurality of clockwise turns and a plurality of counterclockwise turn.

Each of attachment elements 20A-20D may hold elongated tube member 14 at two or more locations to cause elongated tube member 14 to define a non-concentric shape that includes a plurality of clockwise turns and a plurality of counterclockwise turns. As depicted in FIG. 1, the shape may be a serpentine shape, a meandering shape, or an S-curve shape, such that elongated. The shape of elongated tube member 14 may also include any other of the shapes of this disclosure, as well as any other shape with a plurality of clockwise turns and a plurality of counterclockwise turns. By packaging elongated medical device 12 in a shape that includes a plurality of clockwise turns and a plurality of counterclockwise turns, elongated medical device 12 may experience reduced whipping during medical procedures, e.g., as compared to a packaging shape that holds medical device 12 in a concentric shape. Reduced whipping may speed the time for medical procedures and reduce errors.

Figure 12:
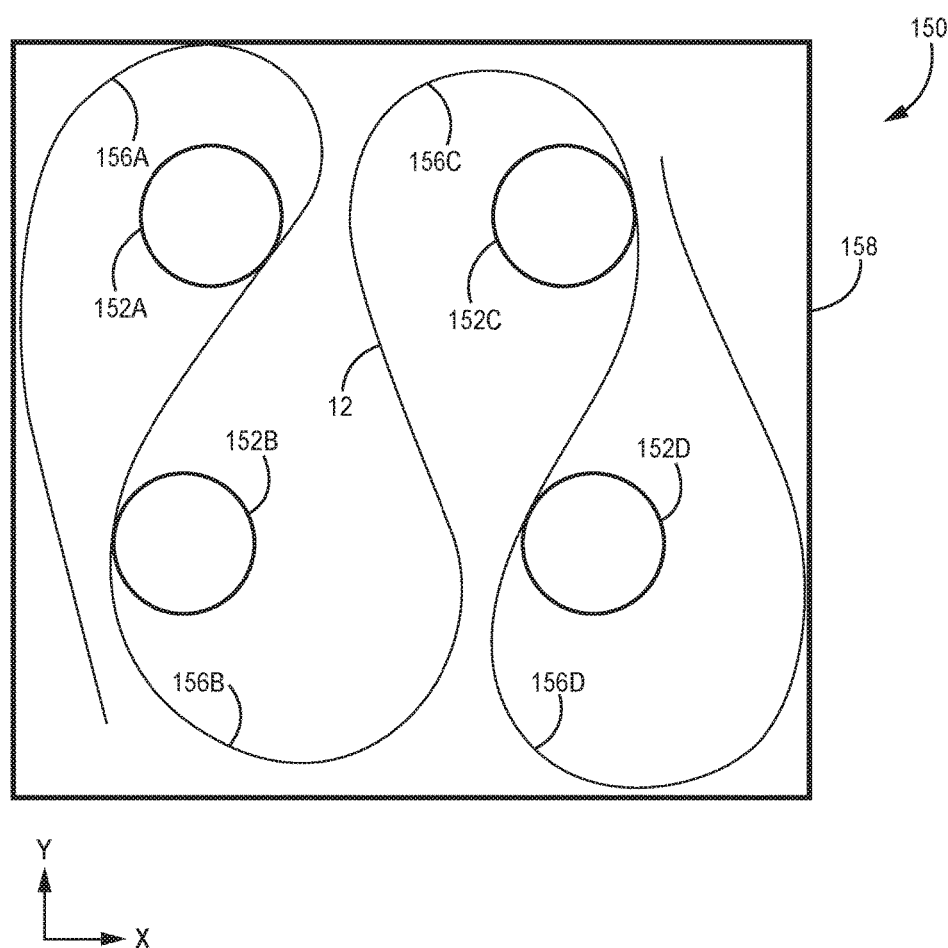
FIG. 12 illustrates an example medical device package including a container and barriers that hold an elongated medical device in a non-concentric shape, which, in the example shown in FIG. 12, is a serpentine shape.

In addition to, or instead of using elongated tube member 14, medical device package 10 may package elongated medical device 12 such that elongated medical device 12 defines a shape that includes a plurality of clockwise turns and a plurality of counterclockwise turns by one or more other various means. In some examples, medical device package 10 may include a container defining a recess or the like for receiving medical device 12, where the recess defines a plurality of clockwise turns and a plurality of counterclockwise turns, as depicted in FIG. 12. Elongated medical device 12 may be placed in the elongated space for shipment and storage. As another example, medical device package 10 may include a container including barriers that are configured to hold and store elongated medical device 12 in a shape that includes a plurality of clockwise turns and a plurality of counterclockwise turns, such as an S-shape or a serpentine shape. The container with the elongated space may or may not include elongated tube member 14. In some examples, medical device package 10 may include tape, glue, or other means of causing elongated tube member 14 to hold elongated medical device 12 in a shape that includes a plurality of clockwise turns and a plurality of counterclockwise turns.

Figure 2:
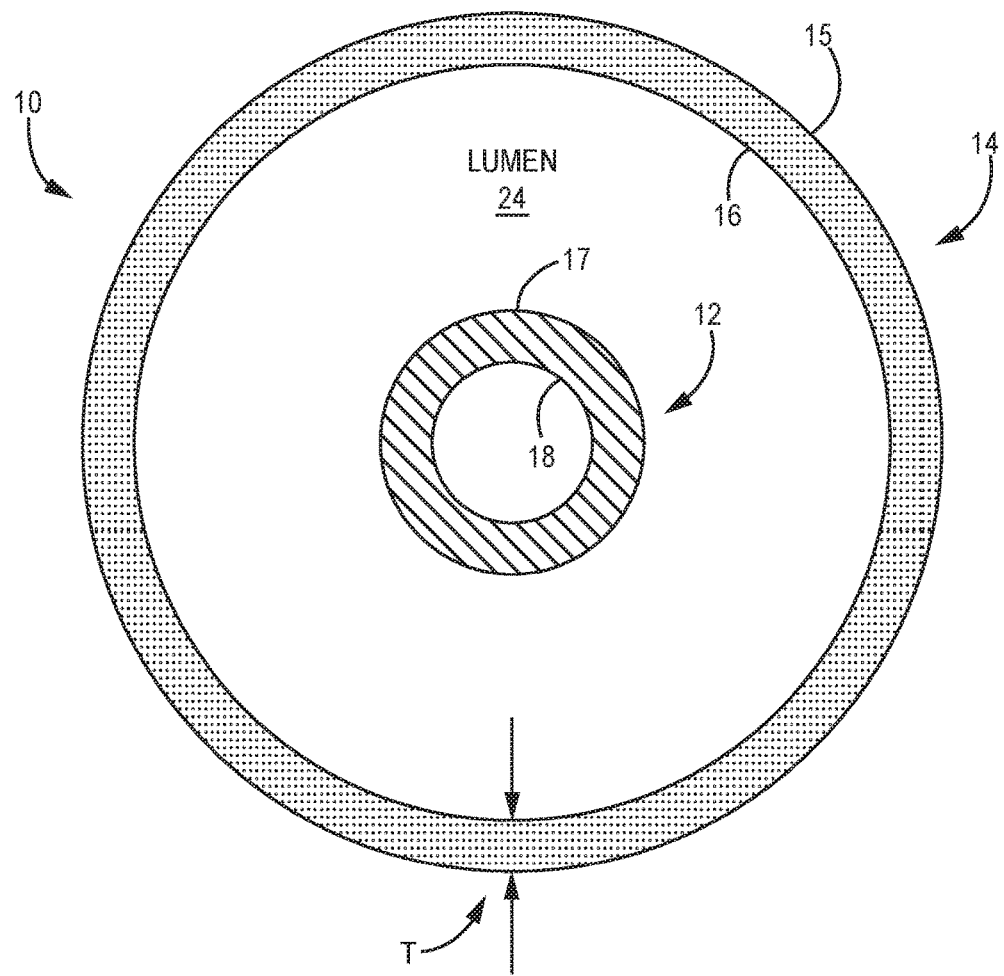
FIG. 2 is a cross-sectional view of the medical device package of FIG. 1, where the cross-section is taken in a direction orthogonal to a longitudinal axis of the elongated medical device.

FIG. 2 is a cross-sectional view of the medical device package 10 of FIG. 1, where the cross-sectional view is perpendicular to a longitudinal axis of the elongated medical device 12 housed in a lumen of elongated tube member 14. The longitudinal axis of elongated medical device 12 may run along the length of elongated medical device 12. The cross-sectional view of FIG. 2 may correspond to a cross-sectional view at line A-A in FIG. 1, or any other location along elongated tube member 14 in which elongated medical device 12 is inside elongated tube member 14.

Elongated tube member 14 may include wall 16 that defines lumen 24. Outer surface 15 of wall 16 is also shown in FIG. 2. Outer surface 15 may, in some examples, define the outermost surface of medical device package 10. Attachment elements 20A-20D may attach to outer surface 15 and hold elongated tube member 14. Lumen 24 may be configured to receive elongated medical device 12 and may include a diameter of less than 3 mm in some examples. Wall 16 can have any suitable thickness for providing the desired level of structural integrity to elongated tube member 14. For example, wall 16 may have a thickness T of about 0.18 inches (approximately 4.57 mm) to about 0.23 inches (approximately 5.84 mm).

In the example shown in FIG. 2, elongated medical device 12 includes wall 18 with outer surface 17 that is enclosed within lumen 24. Elongated medical device 12 may have a smaller cross-sectional dimension than lumen 24, and the size of the cross-sectional dimension may depend on a desired size of medical device package 10, where the cross-section is taken in a direction perpendicular to the respective device 12 or elongated tube member 14. In some examples, wall 18 of medical device 12 may define a lumen configured to receive a guidewire, a stent, and/or any other suitable component for delivery to or retrieval from the vasculature of a patient. However, elongated medical device 12 can include other configurations in other examples, e.g., may define multiple lumens, may not define any lumens, or may have another suitable cross-sectional shape. Elongated medical device 12 and elongated tube member 14 may include any suitable cross-sectional shape. FIG. 2 depicts elongated medical device 12 and elongated tube member 14 with circular cross-sectional shapes, but either or both of elongated medical device 12 and elongated tube member 14 may include any other suitable cross-sectional shape, such as, but not limited to, elliptical, rectangular, square, and the like.

FIG. 2 depicts elongated medical device 12 as being positioned near the center of lumen 24 (e.g., such that medical device 12 and tube member 14 are coaxial). However, in other examples, elongated medical device 12 may be positioned anywhere in lumen 24. For example, at least part of outer surface 17 of medical device 12 may contact wall 16 of elongated tube member 14, e.g., around the clockwise and/or counterclockwise turns defined by elongated tube member 14, or where medical device 12 rests on the inner surface of wall 16, e.g., due to gravitational forces.

Figure 3:
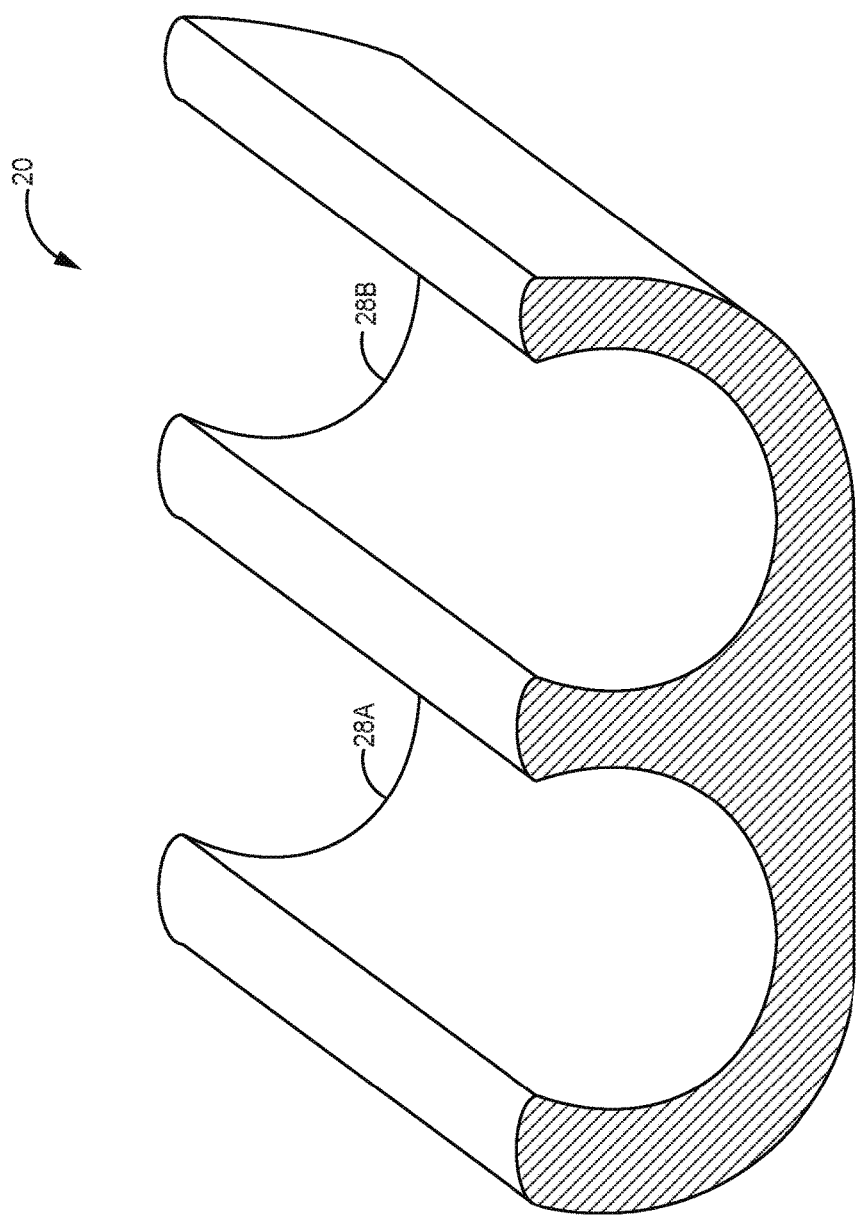
FIG. 3 illustrates an example attachment element configured to hold an elongated tube member of a medical device package at two or more locations.

FIG. 3 illustrates an example attachment element 20 configured to hold an elongated tube member 14 of medical device package 10 at two or more locations. Attachment element 20 may also include any other suitable shape not shown in FIG. 3. In some examples, in order to package medical device 12 in a non-concentric shape, such as a shape including a plurality of clockwise turns and a plurality of counterclockwise turns, attachment element 20 may be configured to connect directly to elongated medical device 12 instead of or in addition to connecting to elongated tube member 14.

Attachment element 20, as depicted in FIG. 3, includes a discrete component configured to mechanically attach to elongated tube member 14, e.g., by interference fit or an adhesive. Attachment element 20 may include structure for connecting to and holding elongated tube member 14 at two or more locations. FIG. 3 depicts attachment element 20 as including structure for connecting to elongated tube member 14 at two locations. This structure may include semicircular spaces 28A and 28B, which may include openings configured to receive a width of elongated tube member 14 (measured in a direction orthogonal to the longitudinal axis of elongated tube member 14). In some examples, attachment element 20 may include more than two or fewer than two semicircular spaces or any other suitable connection mechanism.

The structure of attachment element 20 may include a snapping mechanism whereby elongated tube member 14 is placed into and held by one of semicircular spaces 28A, 28B of attachment element 20. The material of attachment element 20 may be flexible such that when elongated tube member 14 is pressed into one of semicircular spaces 28A, 28B of attachment element 20, the material of attachment element 20 flexes outward such that the opening of one of semicircular spaces 28A, 28B is large enough to receive elongated tube member 14. When elongated tube member 14 is inside semicircular space 28A or 28B, attachment element 20 may return to the shape depicted in FIG. 3 and hold elongated tube member 14 in place. In some examples, semicircular spaces 28A, 28B of attachment element 20 may include a radius of curvature that is approximately equal to or slightly larger than a radius of outer surface 15 of elongated tube member 14. This may allow attachment element 20 to snugly fit with elongated medical tube member 14.

Attachment element 20 may include a variety of other structures and/or materials in combination with or in the alternative to the structure depicted in FIG. 3. In some examples, attachment element 20 may be formed onto elongated tube member 14. Attachment element 20 may be formed from any suitable material, such as, but not limited to, a polymer such as a medium density polyethylene (HDPE), an adhesive like tape, paste, glue, or heat shrunk material. In some examples, attachment element 20 may include a fastening element, a clamping element, or a tying element such as string, cable tie, such as a twist-tie, or a zip-tie. Attachment element 20 may include a rigid material or a flexible material that connects to elongated tube member 14.

Figure 4:
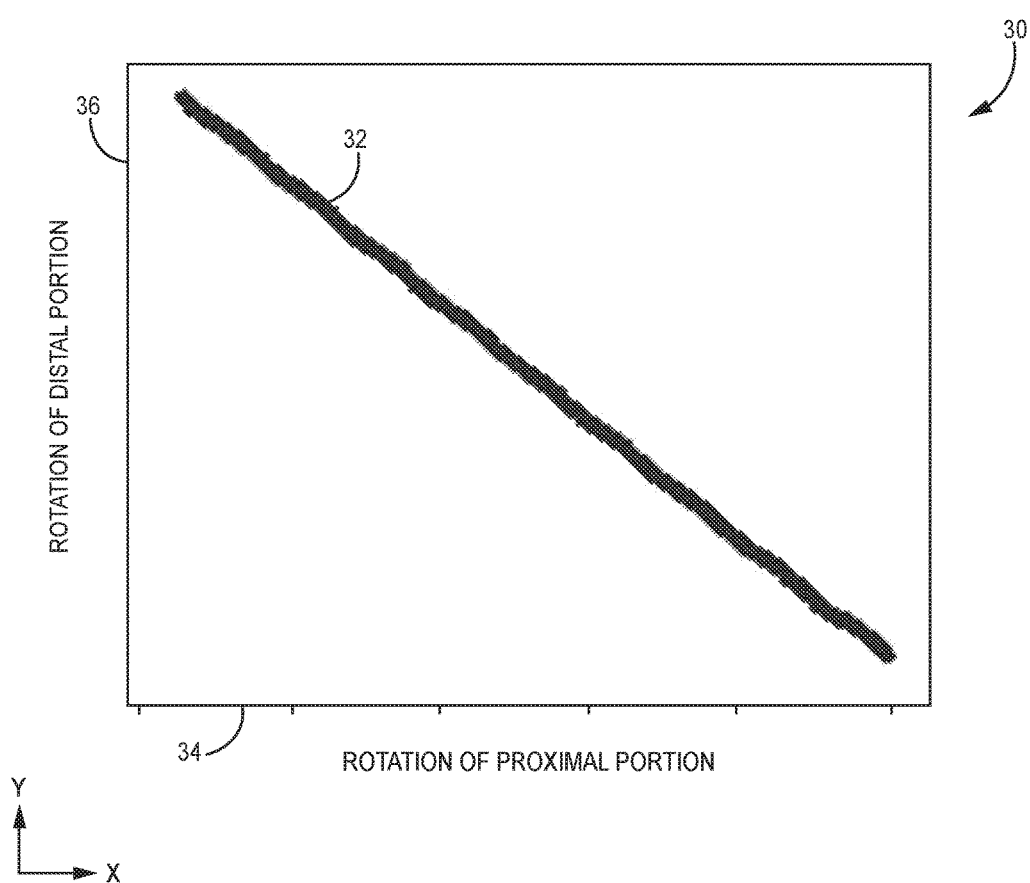
FIG. 4 is a graph illustrating distal rotation of an example elongated medical device packaged in the serpentine shape of FIG. 1 as a function of proximal rotation of the elongated medical device.

FIG. 4 is a graph 30 illustrating distal rotation of an example elongated medical device packaged in the serpentine shape of FIG. 1 as a function of proximal rotation of the elongated medical device when the elongated medical device was outside of a patient and was completely removed from the medical device package. Horizontal axis 34 of graph 30 represents the degree of rotation of a proximal portion of elongated medical device 12 relative to a starting point. Vertical axis 36 of graph 30 represents the degree of rotation of a distal portion of elongated medical device 12 relative to a starting point. Both horizontal axis 34 and vertical axis 36 may include units of degrees or radians.

The distal portion of the test elongated medical device was positioned inside of a test tubing that has the configuration of an example blood vessel of a patient when the proximal portion of the test elongated medical device, positioned outside of the test tubing, was rotated. Line 32 shows an approximately linear relationship between the rotation of the proximal portion and the rotation of the distal portion of the test elongated medical device. This indicates that the rotation of the distal portion of the elongated medical device packaged in a serpentine shape was substantially proportional (e.g., proportional or nearly proportional) to the rotation of the proximal portion of the elongated medical device when the rotational force was applied to the proximal portion. Graph 30 may depict approximately nine full rotations of the proximal portion and the distal portion of elongated medical device 12.

In some examples, medical device package 10 may include package dimensions of width 26A of about 28 cm in the x-axis direction by height 26B of about 28 cm in the y-axis direction, which is approximately eleven inches by eleven inches, as shown in FIG. 1 by width 26A and height 26B. For these package dimensions, elongated tube member 14 may include a radius of curvature of approximately 2.317 inches, or approximately 59 mm, for each of turns 22A-22D in elongated tube member 14. In some examples, the S-value for elongated medical device 12 that is stored in elongated tube member 14 with these dimensions may be 0.0301326. An S-value may represent the standard error of a regression line fitted to graph 30. In general, an S-value may measure how closely a regression line fits a dataset including two variables, which may include the rotation of the proximal portion (x-axis of graph 30) and the rotation of the distal portion (y-axis of graph 30) of elongated medical device 12. As applied to medical device package 10, an S-value may measure how closely the rotation of the distal portion tracks the rotation of the proximal portion when the rotational force is applied to the proximal portion.

The S-value may also measure the smoothness of the rotation of the distal portion. For an S-value of zero, a rotation of k degrees of the proximal portion would be expected to cause a rotation of k degrees of the distal portion. For a nonzero S-value, a rotation of k degrees of the proximal portion would not necessarily cause a rotation of k degrees of the distal portion.

$$S\text{-value} = \sqrt{\frac{1}{N}\sum(\theta_d - \theta_p)^2} \qquad (1)$$

The formula for the S-value is shown in equation (1). N represents the number of measurements of the angular position ($\theta_p$) of the proximal portion of elongated medical device 10. To calculate the S-value, the difference between each measurement of the angular position of the proximal portion of elongated medical device 10 and the respective measurement of the angular position ($\theta_d$) of the distal portion may be squared. The squares may be summed and divided by the number of measurements (N), and the S-value for the dataset may be equal to the square root of the resulting quantity. In some examples, $\theta_p$ may be replaced in equation (1) by an estimated value of $\theta_d$ calculated using a regression line fitted to line 32.

Table I presents experimental results for the medical device packages of FIGS. 1,5, 7-10 and other dimensions of medical device packages not depicted in FIGS. 1-11. The dimensions of a medical device package shown in Table I may be the length and width of the package when the package is lying on a flat horizontal surface. For example, the dimensions of medical device package 10 depicted in FIG. 1 may be height 26B (28 mm) by width 26A (28 mm).

TABLE I

Experimental results for S-values.

| Shape | FIG. | Dimensions (cm) | Hoop radius (cm) | S-value |
|---|---|---|---|---|
| Serpentine | 1 | 28 × 28 | 5.885 | 0.030133 |
| Serpentine | 5 | 28 × 24 | 5.885 | 0.046321 |
| Serpentine | | 10 × 32 | 1.3498 | 0.243483 |
| Serpentine | | 10 × 19 | 1.3498 | 0.155279 |
| Serpentine | | 15 × 30 | 2.4313 | 0.228603 |
| Serpentine | | 15 × 20 | 2.4313 | 0.262222 |
| Serpentine | | 20 × 30 | 3.8621 | 0.155713 |
| Serpentine | | 20 × 19 | 3.8621 | 0.141109 |
| Serpentine | | 25 × 27 | 3.8621 | 0.149938 |
| Serpentine | | 25 × 21 | 3.8621 | 0.212433 |
| Continuous figure-eight | 7 | 12 × 31 | 5.230 | 0.152626 |
| Figure-eight | 8 | 17 × 33 | 6.876 | 0.103794 |
| Tear-drop | 9 | 30 × 41 | 9.790 | 0.106955 |
| Loop | 10 | 19 × 19 | 9.326 | 0.2005 |

In Table I, the hoop radius may be the radius of curvature of one or more of the turns of the medical device package. For example, as shown in Table I, the radius of curvature (shown in the "Hoop Radius" column in Table I) of turns 22A-22D of elongated tube member 14 shown in FIG. 1 may be approximately 59 mm. In some examples, the radius of curvature in Table I may be the shortest radius of curvature or the average radius for the medical device package. For example, turn 22A of medical device package 10 may include a shorter radius of curvature than turn 22B. In other examples, the radius of curvature listed in Table I may be the average radius of curvature for all of turns 22A-22D. In some examples, the radius of curvature of turns 22A-22D of elongated tube member 14 may be more about 4 cm to about 8 cm. In some examples, the radius of curvature of turns 22A-22D of elongated tube member 14 may be about 2 cm to about 15 cm. In some cases, larger radii of curvature may be desirable for longer elongated tube members, for elongated tube members with fewer turns, and/or for thicker elongated tube members.

In some examples, a medical device package may include a different shape than the serpentine shape of elongated tube member 14 depicted in FIG. 1. For example, a medical device package may include a non-concentric shape, a serpentine shape, a meandering shape, an S-shape, a pretzel shape, and/or a figure-eight shape.

Figure 5:
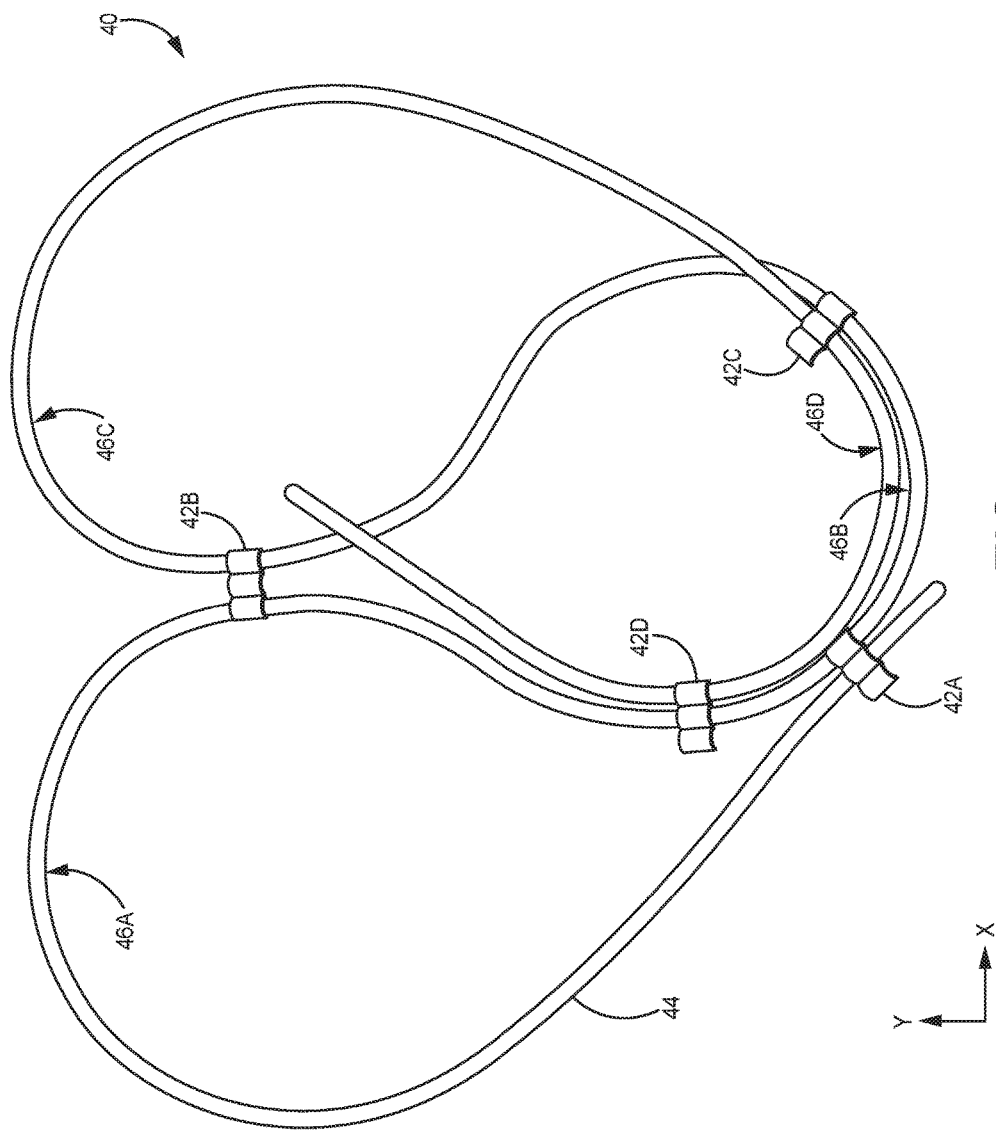
FIG. 5 illustrates another example medical device package configured to hold an elongated medical device in a serpentine shape.

FIG. 5 illustrates another example medical device package 40 configured to hold an elongated medical device in a serpentine shape. Medical device package 40 may include elongated tube member 44 and attachment elements 42A-42D. Elongated tube member 44 and attachment elements 42A-42D may be similar in function and operation to elongated tube member 14 and attachment elements 20A-20D of FIGS. 1 and 3. In other examples, medical device package 40 may not include attachment elements 42A-42D, and, rather, elongated tube member 44 may be held in the serpentine shape without the aid of attachment elements 42A-42D, e.g., due to the stiffness of the material from which elongated tube member 44 is formed.

Elongated tube member 44 may include a different shape than elongated tube member 14 in FIG. 1. Elongated tube member 44 may include a non-concentric pretzel shape or a non-concentric heart shape with two loops on one side, such as turns 46A and 46C, and one loop on the other side, such as turns 46B and 46D that may at least partially overlap. Turn 46B of elongated tube member 44 may at least partially overlap turn 46D of elongated tube member 44. Although FIG. 5 depicts elongated tube member 44 crossing itself, overlapping may not necessarily include elongated tube member 44 crossing itself. For example, elongated tube member 104 in FIG. 10 includes overlapping turns without necessarily including elongated tube member 104 crossing itself. For example, elongated tube member 44 may define clockwise turn 46A between attachment elements 42A, 42B, followed by counter-clockwise turn 46B between attachment elements 42D, 42C. Elongated tube member 44 may then define clockwise turn 46C between attachment elements 42B, 42C, followed by clockwise turn 46D between attachment elements 42C, 42D. In some examples, elongated tube member 44 may include fewer or more turns than depicted in FIG. 5.

Turn 46A may be adjacent to turn 46B, turn 46B may be adjacent to turns 46A and 46C, and turn 46C may be adjacent to turns 46B and 46D. Thus, even though turn 46B of elongated tube member 44 at least partially overlaps turn 46D of elongated tube member 44, turns 46B and 46D may not be "adjacent" as that term is used in this disclosure because turn 46C may be positioned between turns 46B and 46D. Elongated tube member 44 may include alternating turns such that, for example, turn 46C may be clockwise and turns 46B and 46D may be counterclockwise and adjacent to turn 46C.

Each of turns 46A-46D may have the same radius of curvature in some examples. In other examples, however, at least two of the turns 46A-46D may have different radii of curvature. In some examples, medical device package 40 may include a height in the y-axis direction of about 28 cm and a width in the x-axis direction of about 24 cm.

Figure 6:
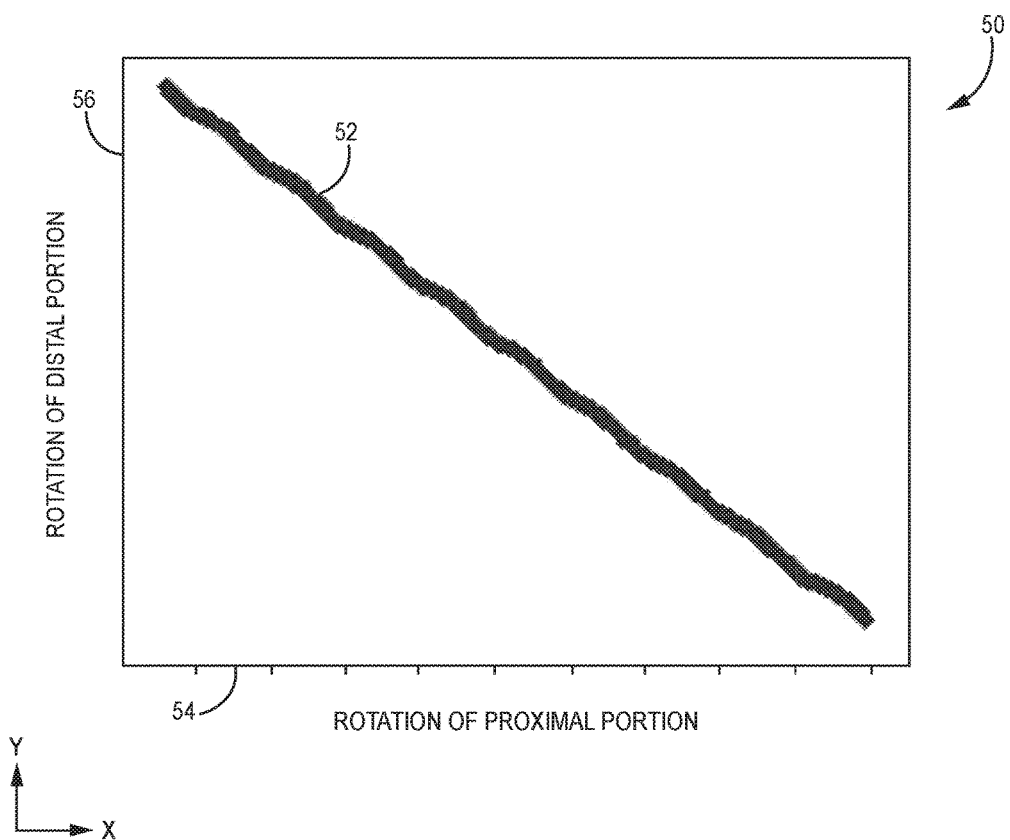
FIG. 6 is a graph illustrating distal rotation of an example elongated medical device packaged in the serpentine shape of FIG. 5 as a function of proximal rotation of the elongated medical device.

FIG. 6 is a graph 50 illustrating distal rotation of an example elongated medical device packaged in the second serpentine shape of FIG. 5 as a function of proximal rotation of the elongated medical device when the elongated medical device was outside of a patient and was completely removed from the medical device package. Horizontal axis 54 of graph 50 represents the degree of rotation of a proximal portion of an elongated medical device stored in elongated tube member 44 relative to a starting point. Vertical axis 56 of graph 50 represents the degree of rotation of a distal portion of the elongated medical device relative to a starting point. Both horizontal axis 54 and vertical axis 56 may include units of degrees or radians. The distal portion of the test elongated medical device was positioned inside of a test tubing that has the configuration of an example blood vessel of a patient when the proximal portion of the test elongated medical device, positioned outside of the test tubing, was rotated.

Line 52 shows an approximately linear relationship between the rotation of the proximal portion and the rotation of the distal portion of the test elongated medical device. This indicates that the rotation of the distal portion of the elongated medical device packaged in a serpentine shape was substantially proportional (e.g., proportional or nearly proportional) to the rotation of the proximal portion of the elongated medical device when the rotational force was applied to the proximal portion. Graph 50 may depict approximately nine full rotations of the proximal portion and the distal portion of the elongated medical device.

In some examples, medical device package 40 may include package dimensions in the x-axis direction of about 24 cm by about 28 cm in the y-axis direction, which is approximately 9.5 inches by 11 inches. For these package dimensions, elongated tube member 44 may include a radius of curvature of approximately 2.317 inches or approximately 59 cm. In some examples, the S-value for the elongated medical device stored in elongated tube member 44 with these dimensions may be 0.0463207. The S-value for medical device package 40 may be higher than the S-value for medical device package 10 because line 52 may include greater deviations from a straight line, as compared to line 32 in FIG. 4. However, the elongated medical device stored in elongated tube member 44 of medical device package 40 may show a reduced tendency to whip, as compared to an elongated medical device stored in a concentric package. The alternating turns 46A-46D of elongated tube member 44 and the non-concentric arrangement of elongated tube member 44 may reduce the tendency of elongated medical device stored therein to whip.

Figure 7:
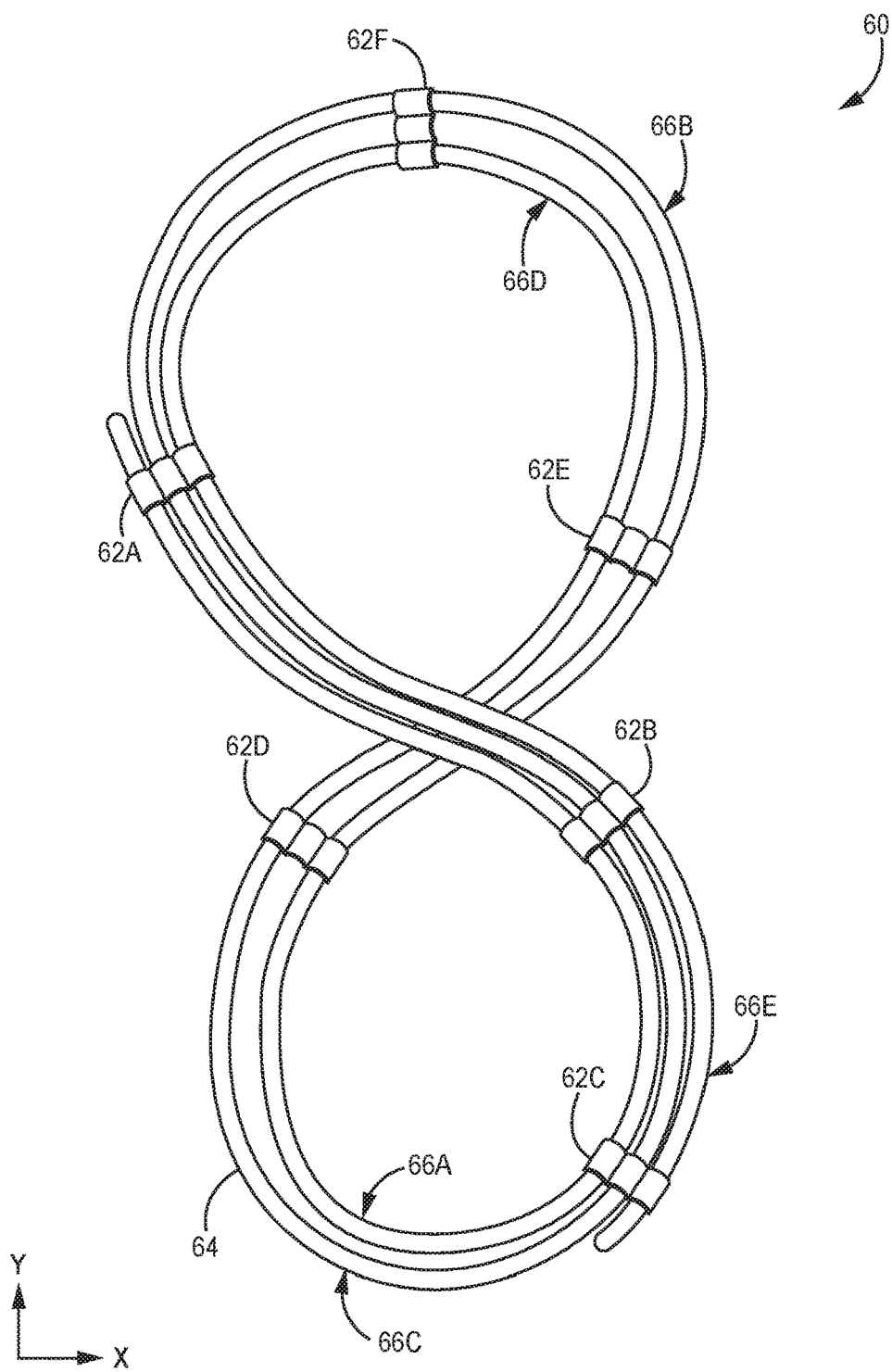
FIG. 7 illustrates an example medical device package configured to hold an elongated medical device in a non-concentric shape, which, in the example shown in FIG. 7, is a continuous figure-eight shape.

FIG. 7 illustrates an example medical device package 60 configured to hold an elongated medical device in a non-concentric shape, which, in the example shown in FIG. 7, is a continuous figure-eight shape. Medical device package 60 may include elongated tube member 64 and attachment elements 62A-62F. Elongated tube member 64 and attachment elements 62A-62F may be similar in function and operation to elongated tube member 14 and attachment elements 20A-20D of FIGS. 1 and 3. In other examples, medical device package 60 may not include attachment elements 62A-62F, and, rather, elongated tube member 64 may be held in the serpentine shape without the aid of attachment elements 62A-62F, e.g., due to the stiffness of the material from which elongated tube member 64 is formed.

In the continuous figure-eight shape, elongated tube member 64 may define clockwise turns 66A, 66C, and 66E between attachment elements 62A and 62D, followed by counter-clockwise turn 66B, 66D between attachment elements 62E and 62A. In some examples, elongated tube member 64 may include fewer or more turns than depicted in FIG. 7. Turn 66A of elongated tube member 64 may at least partially overlap turns 66C and 66E of elongated tube member 64. Turn 66B of elongated tube member 64 may at least partially overlap turn 66D of elongated tube member 64. Medical device package 60 may include two loops that do not overlap, where a first loop is formed by turns 66A, 66C, and 66E of elongated tube member 64, and a second loop is formed by turns 66B and 66D of elongated tube member 64.

Thus, even though turn 66B of elongated tube member 4 at least partially overlaps turn 66D of elongated tube member 64, turns 66B and 66D may not be "adjacent" as that term is used in this disclosure because turn 66C may be positioned between turns 66B and 66D. Elongated tube member 64 may include alternating turns such that, for example, turn 66C may be clockwise and turns 66B and 66D may be counterclockwise and adjacent to turn 66C. Each of turns 66A-66E may have the same radius of curvature in some examples. In other examples, however, at least two of turns 66A-66E may have different radii of curvature.

In some examples, the S-value for the elongated medical device stored in elongated tube member 64 of medical device package 60 may be 0.152626. This S-value may indicate a greater tendency for elongated tube member 64 to whip, as compared to elongated tube members 14, 44. However, the elongated medical device stored in elongated tube member 64 of medical device package 60 may show a reduced tendency to whip, as compared to an elongated medical device stored in a concentric package. The alternating turns 66A-66E of elongated tube member 64 and the non-concentric arrangement of elongated tube member 64 may reduce the tendency of elongated medical device stored therein to whip.

Figure 8:
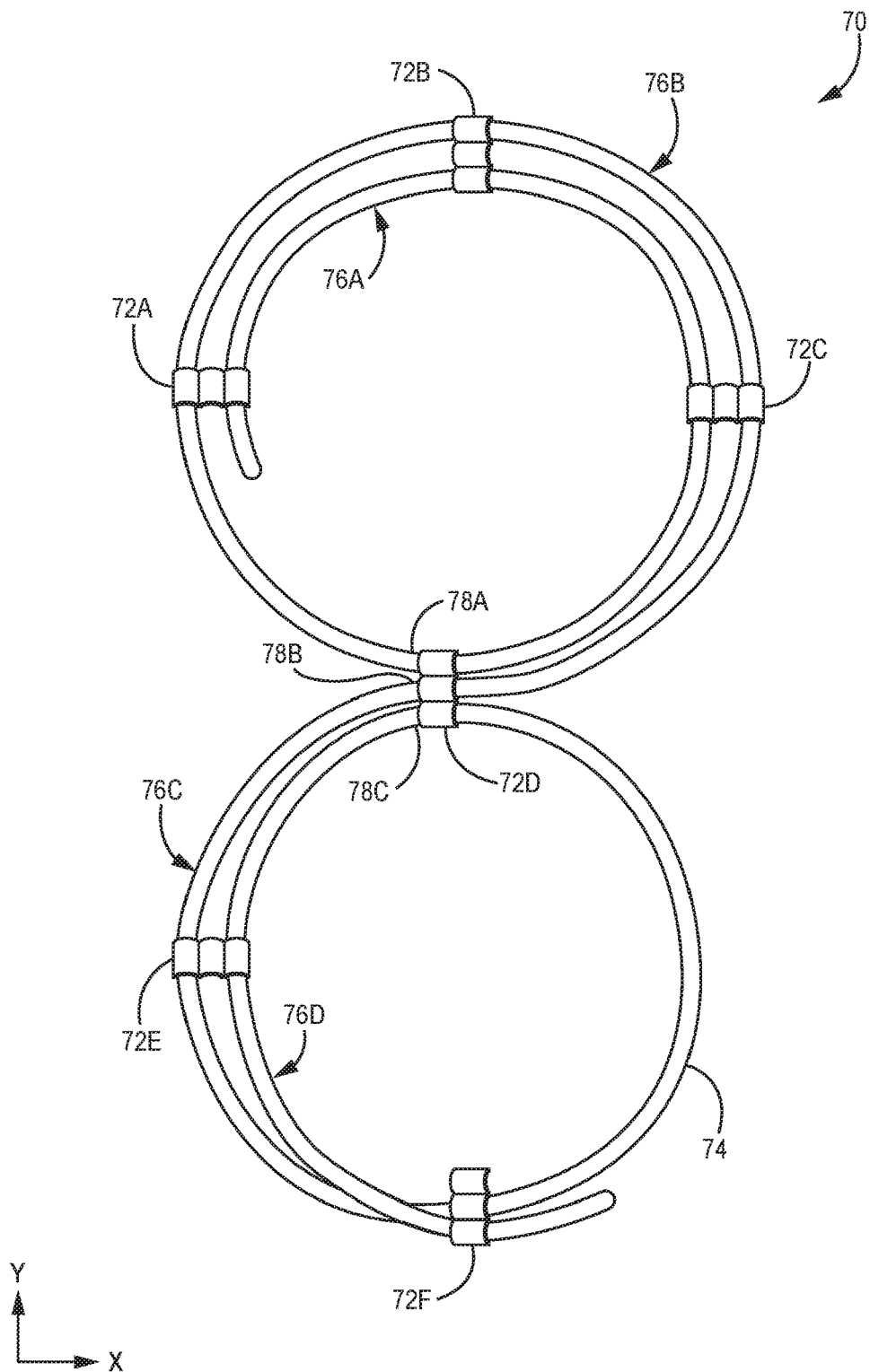
FIG. 8 illustrates an example medical device package configured to hold an elongated medical device in another example figure-eight shape.

FIG. 8 illustrates an example medical device package 70 configured to hold an elongated medical device in another example figure-eight shape. Medical device package 70 may include elongated tube member 74 and attachment elements 72A-72F. Elongated tube member 74 and attachment elements 72A-72F may be similar in function and operation to elongated tube member 14 and attachment elements 20A-20D of FIGS. 1 and 3. For example, attachment element 72D may be attached to elongated tube member 74 at three locations 78A-78C. Location 78A may be adjacent to location 78B along elongated tube member 74 because locations 78A, 78B are separated by turn 76B of elongated tube member 74. Location 78B may be adjacent to location 78C along elongated tube member 74 because locations 78B, 78C are separated by turn 76C of elongated tube member 74. In other examples, medical device package 70 may not include attachment elements 72A-72F, and, rather, elongated tube member 74 may be held in the serpentine shape without the aid of attachment elements 72A-72F, e.g., due to the stiffness of the material from which elongated tube member 74 is formed.

Elongated tube member 74 defines clockwise turns 76A and 76B between attachment elements 72A and 72D, followed by counter-clockwise turns 76C and 76D between attachment elements 72D and 72F. In some examples, elongated tube member 74 may include fewer or more turns than depicted in FIG. 8. Turn 76A of elongated tube member 74 may at least partially overlap turn 76B of elongated tube member 74. Turn 76C of elongated tube member 74 may at least partially overlap turn 76D of elongated tube member 74. Medical device package 70 may include two loops that do not overlap, where a first loop is formed by turns 76A and 76B of elongated tube member 74, and a second loop is formed by turns 76C and 76D of elongated tube member 74. Turn 76A may be adjacent to turn 76B, turn 76B may be adjacent to turn 76C, and turn 76C may be adjacent to turn 76D. Each of turns 76A-76D may have the same radius of curvature in some examples. In other examples, however, at least two of turns 76A-76D may have different radii of curvature.

In some examples, the S-value for the elongated medical device stored in elongated tube member 74 of medical device package 70 may be 0.103791. This S-value may indicate a greater tendency for elongated tube member 74 to whip, as compared to elongated tube members 14, 44.

However, the elongated medical device stored in elongated tube member 74 of medical device package 70 may show a reduced tendency to whip, as compared to an elongated medical device stored in a concentric package. Clockwise turns 76A, 76B and counterclockwise turns 76C, 76D and the non-concentric arrangement of elongated tube member 74 may reduce the tendency of elongated medical device stored therein to whip.

Figure 9:
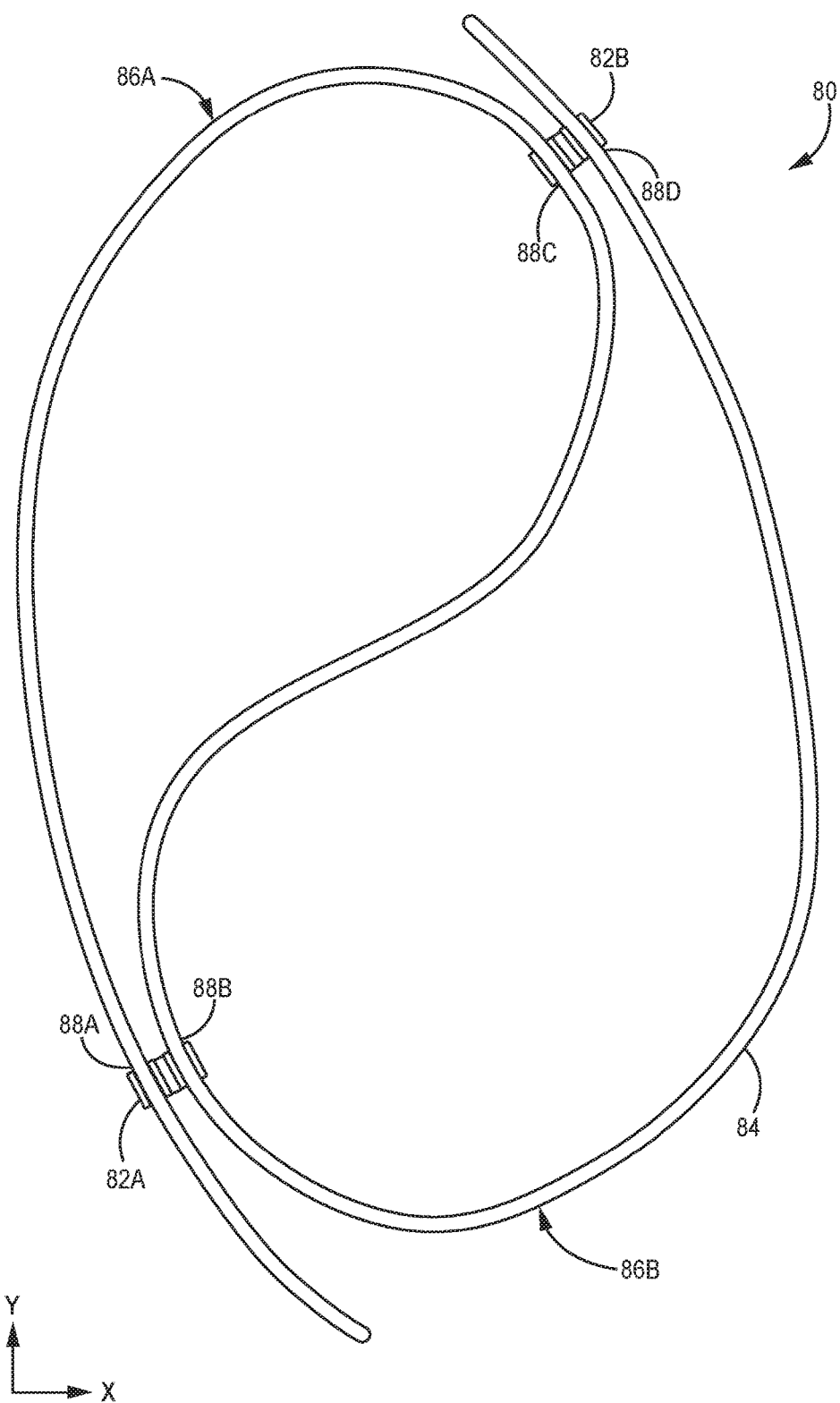
FIG. 9 illustrates an example medical device package configured to hold an elongated medical device in a non-concentric shape, which, in the example shown in FIG. 9, includes one or more tear-drop shapes.

FIG. 9 illustrates an example medical device package 80 configured to hold an elongated medical device in a non-concentric shape, which, in the example shown in FIG. 9, includes one or more tear-drop shapes. Elongated tube member 84 may also include a meandering shape because of alternating clockwise and counterclockwise turns 86A and 86B. Medical device package 80 may include elongated tube member 84 and attachment elements 82A, 82B. Elongated tube member 84 and attachment elements 82A, 82B may be similar in function and operation to elongated tube member 14 and attachment elements 20A-20D of FIGS. 1 and 3. In other examples, medical device package 84 may not include attachment elements 82A, 82B, and, rather, elongated tube member 84 may be held in the serpentine shape without the aid of attachment elements 82A, 82B, e.g., due to the stiffness of the material from which elongated tube member 84 is formed.

Elongated tube member 84 defines clockwise turn 86A between location 88A held by attachment element 82A and location 88B held by attachment element 82A, followed by counter-clockwise turn 86B between location 88C held by attachment element 82B and location 88D held by attachment element 82B. In some examples, elongated tube member 84 may include fewer or more turns than depicted in FIG. 9. In some examples, turn 86A of elongated tube member 84 may partially overlap turn 86B of elongated tube member 84. Elongated tube member 84 may include alternating turns such that, for example, turn 86A may be clockwise and turn 86B may be counterclockwise and adjacent to turn 86A. Each of turns 86A and 86B may have the same radius of curvature in some examples. In other examples, however, at least two of turns 86A and 86B may have different radii of curvature.

In some examples, the S-value for the elongated medical device stored in elongated tube member 84 of medical device package 80 may be 0.106955. This S-value may indicate a greater tendency for elongated tube member 84 to whip, as compared to elongated tube members 14, 44. However, the elongated medical device stored in elongated tube member 84 of medical device package 80 may show a reduced tendency to whip, as compared to an elongated medical device stored in a concentric package. The alternating turns 86A, 86B and the non-concentric arrangement of elongated tube member 84 may reduce the tendency of elongated medical device stored therein to whip.

Figure 10:
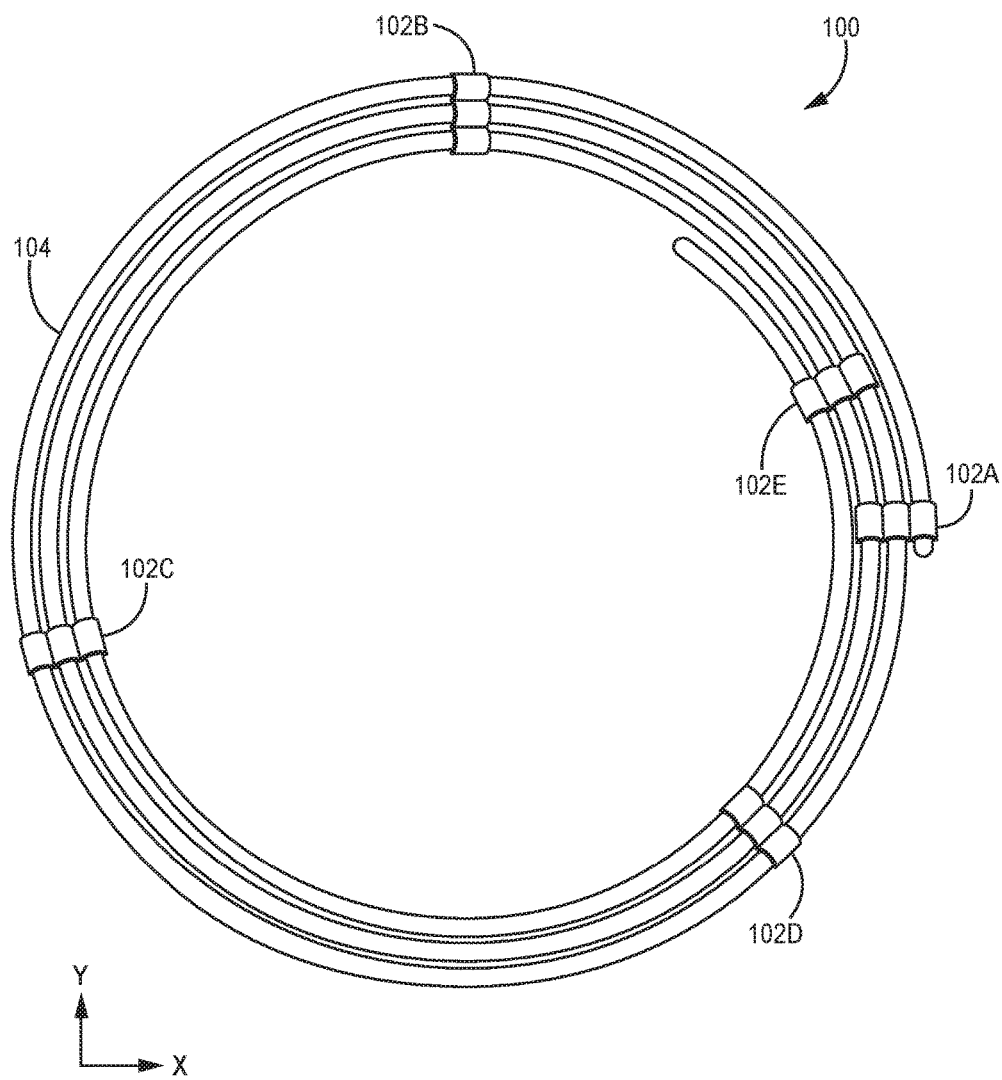
FIG. 10 illustrates an example medical device package configured to hold an elongated medical device in a concentric shape, which is shown in FIG. 10 as a loop shape.

FIG. 10 illustrates an example medical device package 100 configured to hold an elongated medical device in a concentric shape, which is shown in FIG. 10 as a loop shape. Elongated tube member 104 may define a single counter-clockwise turn for approximately three full revolutions at locations held by attachment elements 102A-102E. Elongated tube member 104 may overlap on itself for each revolution even though the overlapping turns of elongated tube member 104 may not necessarily include elongated tube member 104 crossing itself.

Figure 11:
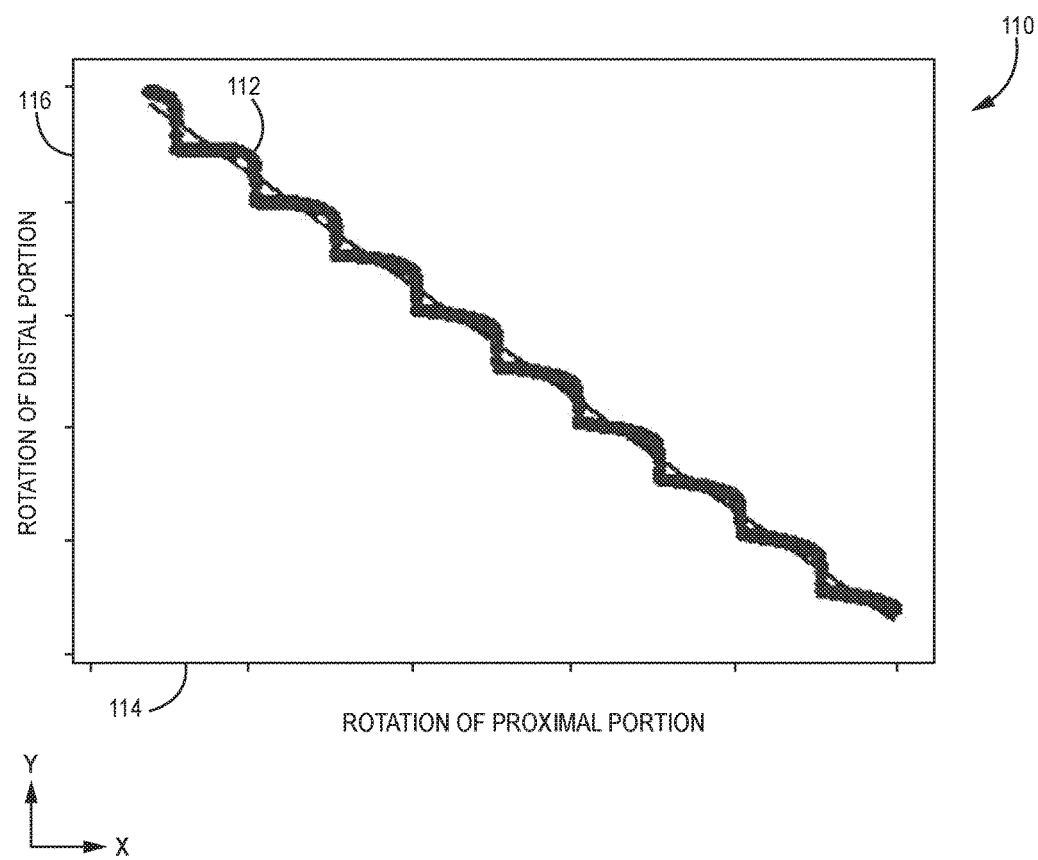
FIG. 11 is a graph illustrating distal rotation of an example elongated medical device packaged in the loop shape of FIG. 10 as a function of proximal rotation of the elongated medical device.

FIG. 11 is a graph 110 illustrating distal rotation of an example elongated medical device packaged in the loop shape of FIG. 10 as a function of proximal rotation of the elongated medical device when the elongated medical device was outside of a patient and was completely removed from the medical device package. Horizontal axis 114 of graph 110 represents the degree of rotation of a proximal portion of an elongated medical device stored in elongated tube member 104 relative to a starting point. Vertical axis 56 of graph 50 represents the degree of rotation of a distal portion of the elongated medical device relative to a starting point. Both horizontal axis 54 and vertical axis 56 may include units of degrees or radians. The distal portion of the test elongated medical device was positioned inside of a test tubing that has the configuration of an example blood vessel of a patient when the proximal portion of the test elongated medical device, positioned outside of the test tubing, was rotated.

Graph 110 may depict approximately nine full rotations of the proximal portion and the distal portion of the elongated medical device. In some examples, the S-value for the elongated medical device stored in elongated tube member 104 of medical device package 100 may be 0.2005. This S-value may indicate a greater tendency for elongated tube member 104 to whip, as compared to elongated tube members 14, 44. As compared to graphs 30 and 50 (FIGS. 4 and 6, respectively), the rotation of the distal portion in graph 100 includes larger deviations from a straight line. The larger deviations may correspond to less proportional rotation of the proximal portion and the distal portion of an elongated medical device stored in elongated tube member 104, as compared to elongated medical device 12 stored in elongated tube member 14. The continuous clockwise turn of elongated tube member 104 may cause less proportional rotation because an elongated medical device may set into the shape of elongated tube member 104.

In some examples, a medical device package may not include attachment elements (e.g., attachment elements 20A-20D shown in FIG. 1) to hold an elongated tube member in a non-concentric shape, but alternatively or additionally may include a container configured to hold elongated medical device 12 in a non-concentric shape. For example, the container may define a space (e.g., a recess) having the desired non-concentric shape, the space being configured to receive elongated medical device 12. For example, the space may be an elongated serpentine-shaped space that includes a plurality of clockwise turns and a plurality of counterclockwise turns or a space with barriers that cause elongated medical device 12 to define a shape that includes a plurality of clockwise turns and a plurality of counterclockwise turns.

FIG. 12 illustrates an example medical device package 150 including a container 158 and barriers 152A-152D that hold an elongated medical device 12 in a non-concentric shape, which, in the example shown in FIG. 12, is a serpentine shape. Container 158 may define a space (e.g., a recess) having the desired non-concentric shape, the space being configured to receive elongated medical device 12. The space may include an open area in which elongated medical device 12 may be positioned for storage and/or shipping. Additionally, or alternatively, the space may also include an inset area that includes a serpentine shape, a meandering shape, and/or another other shape including at least one clockwise turn and at least one counterclockwise turn. For at least the reasons discussed with respect to elongated tube member 14 of FIG. 1, elongated medical device 12 stored in container 158 may show a reduced tendency to whip, as compared to an elongated medical device stored in a concentric package. The alternating turns 156A-156D and the non-concentric arrangement of elongated medical device 12 may reduce the tendency of elongated medical device 12 to whip.

Container 158 may include a box, a tray, or any other suitable configuration with a hollow interior or an elongated space for holding elongated medical device 12. Elongated medical device 12 may be placed in the hollow interior in a manner such that elongated medical device 12 forms a serpentine shape by meandering through barriers 152A-152D. The inner wall of container 158 may also act as a barrier, and the inner wall of container 158 and barriers 152A-152D may cause elongated medical device 12 to form a serpentine shape. Elongated medical device 12 may include four turns 156A-156D that define a serpentine shape or a meandering shape because of alternating clockwise and counterclockwise turns 156A-156D. As depicted in FIG. 12, turns 156A-156D may not overlap. In some examples, elongated medical device 12 may be long enough to include additional turns that may overlap one or more of turns 156A-156D. Each of turns 156A-156D may have the same radius of curvature in some examples. In other examples, however, at least two of turns 156A-156D may have different radii of curvature.

Barriers 152A-152D may be fixed to the inner wall(s) of container 158, or the positions of barriers 152A-152D may be adjustable to cause elongated medical device 12 to form a variety of shapes. In some examples, medical device package 150 may include a container with an elongated space inside the container, where the elongated space includes a plurality of clockwise turns and a plurality of counterclockwise turns. The elongated space may cause elongated medical device 12 to form a shape that is similar to the shape of the elongated space. In some examples, medical device package 150 may include tape, glue, or other means of causing elongated medical device 12 to form a shape that includes a plurality of clockwise turns and a plurality of counterclockwise turns.

In accordance with a technique of this disclosure, elongated tube member 14 defining lumen 24 configured to receive elongated medical device 12 is formed into the desired non-concentric shape. In some examples, elongated tube member 14 may be formed of a polymer such as HDPE using a process such as injection molding, extrusion, blow molding, vacuum forming, compression molding, or any other suitable process.

In some examples, forming elongated tube member 14 into the desired non-concentric shape may include connecting one or more attachment elements 20A-20D to elongated tube member 14 to hold elongated tube member 14 in the non-concentric shape, such as a shape that includes a plurality of clockwise turns and a plurality of counterclockwise turns. Examples of such shapes may include a serpentine shape (e.g., FIGS. 1 and 5), a meandering shape, a figure-eight shape (e.g., FIGS. 7 and 8), a tear-drop shape (e.g., FIG. 9), or any other suitable shape that includes a plurality of clockwise turns and a plurality of counterclockwise turns. For example, attachment element 20A may include a hook, a clip, or an adhesive for connecting to elongated tube member 14 at two or more locations. In some examples, attachment element 20A may include a discrete component, or attachment element 20A may be integrated into elongated tube member 14. As a discrete component, attachment element 20A may be removable from elongated tube member 14. As an integrated component, attachment element 20A may be formed from the same material as elongated tube member 14. Attachment element 20A may also be friction-fitted to elongated tube member 14.

In some examples, after forming elongated tube member 14 of medical device package 10 into the desired non-concentric shape, the method of this disclosure may further include introducing elongated medical device 12 into lumen 24 of elongated tube member 14. For example, a user may introduce a distal or proximal portion of elongated medical device 12 into lumen 24 and push elongated medical device 12 fully or partially into lumen 24.

Elongated medical device 14 may, in some cases, assume the shape of elongated tube member 12. For example, during sterilization, elongated medical device 14 may assume or maintain the shape of the package. In some cases, the assumed serpentine shape may impact the ease of delivery of elongated medical device 14 in a patient. For example, medical device package 10 may impart a curvature to elongated medical device 14. This curvature may adversely impact the navigability of elongated medical device 14 within the vasculature of a patient, such as by causing a "whipping" effect during rotation of elongated medical device 14. The non-concentric shape of medical device package 10 may help minimize or even eliminate the adverse effects of medical device storage on the navigability of elongated medical device 14, as compared to medical device packages that store elongated medical devices in a concentric configuration, such as medical device package 100 depicted in FIG. 10.

Various examples of the disclosure have been described. Any combination of the described systems, operations, or functions is contemplated. These and other examples are within the scope of the following claims.

What is claimed is:
1. A medical device package comprising:
   an elongated tube member defining a lumen, wherein the lumen is configured to receive an elongated medical device; and
   an attachment element configured to hold a first portion of the elongated tube member to a second portion of the elongated tube member such that the elongated tube member defines a shape that includes a plurality of clockwise turns and a plurality of counterclockwise turns.
2. The medical device package of claim 1, wherein the attachment element is configured to hold the elongated tube member at three or more locations such that the elongated tube member defines the shape that includes the plurality of clockwise turns and the plurality of counterclockwise turns.
3. The medical device package of claim 1, wherein the attachment element comprises two or more clips configured to connect to an outer wall of the elongated tube member.
4. The medical device package of claim 1, wherein a distance between a first location of the first portion and a second location of the second portion is about 10 centimeters to about 20 centimeters along the elongated tube member, and the first location and the second location are adjacent to each other when the elongated tube member defines the shape.
5. The medical device package of claim 1, wherein the shape is a serpentine shape.
6. The medical device package of claim 5, wherein the serpentine shape comprises two or more turns, and a radius of curvature for each turn of the two or more turns is more than two centimeters and less than fifteen centimeters.
7. The medical device package of claim 5, wherein the radius of curvature for each turn of the two or more turns is more than four centimeters and less than eight centimeters.

8. The medical device package of claim 1, wherein the shape includes a plurality of alternating clockwise turns and counterclockwise turns.

9. The medical device package of claim 1, wherein a clockwise turn of the plurality of clockwise turns is adjacent to a counterclockwise turn of the plurality of counterclockwise turns.

10. The medical device package of claim 1, wherein the shape is a figure-eight shape.

11. The medical device package of claim 1, wherein the elongated tube member comprises a polymer.

12. The medical device package of claim 11, wherein the polymer is high-density polyethylene.

13. The medical device package of claim 1, wherein the elongated tube member defines two or more loops that do not overlap.

14. The medical device package of claim 1, wherein the elongated tube member comprises a length of about 100 centimeters to about 300 centimeters.

15. The medical device package of claim 1, wherein the lumen has a diameter of less than about 3 millimeters.

16. The medical device package of claim 1, further comprising the elongated medical device received within the elongated tube member.

17. The medical device package of claim 16, wherein the elongated medical device comprises a catheter.

18. The medical device package of claim 16, wherein the elongated medical device is fully received within the elongated tube member.

19. A medical device package comprising:
an elongated tube member defining a lumen, wherein the lumen is configured to receive an elongated medical device; and
an attachment element configured to hold a first portion of the elongated tube member to a second portion of the elongated tube member such that the elongated tube member defines a non-concentric shape.

20. The medical device package of claim 19, wherein the attachment element is configured to hold the elongated tube member at three or more locations such that the elongated tube member defines the non-concentric shape.

21. The medical device package of claim 19, wherein the non-concentric shape is a serpentine shape or a figure-eight shape.

22. The medical device package of claim 19, wherein the elongated tube member defines two or more loops that do not overlap.

23. A medical device package configured to store an elongated medical device, wherein the medical device package comprises:
an elongated tube member defining a lumen, wherein the lumen is configured to receive the elongated medical device; and
attachment means connecting to the elongated tube member, wherein the attachment means is configured and positioned to hold a first portion of the elongated tube member to a second portion of the elongated tube member such that the elongated tube member defines a shape that includes a plurality of clockwise turns and a plurality of counterclockwise turns.

24. A method comprising:
forming a medical device package comprising an elongated tube member defining a lumen that is configured to receive an elongated medical device; and
attaching an attachment element to a first portion of the elongated tube member and a second portion of the elongated tube member such that the elongated tube member defines a shape that includes a plurality of clockwise turns and a plurality of counterclockwise turns.

25. The method of claim 24, wherein the attachment element comprises a first attachment element, the method further comprising attaching a second attachment element to the elongated tube member to hold the elongated tube member in the shape that includes the plurality of clockwise turns and the plurality of counterclockwise turns.

26. The method of claim 24, wherein the shape is a serpentine shape or a figure-eight shape.

27. The method of claim 24, wherein the elongated tube member defines two or more loops that do not overlap.

28. The method of claim 24, further comprising introducing the elongated medical device in the lumen of the elongated tube member.

* * * * *